Figure 1:
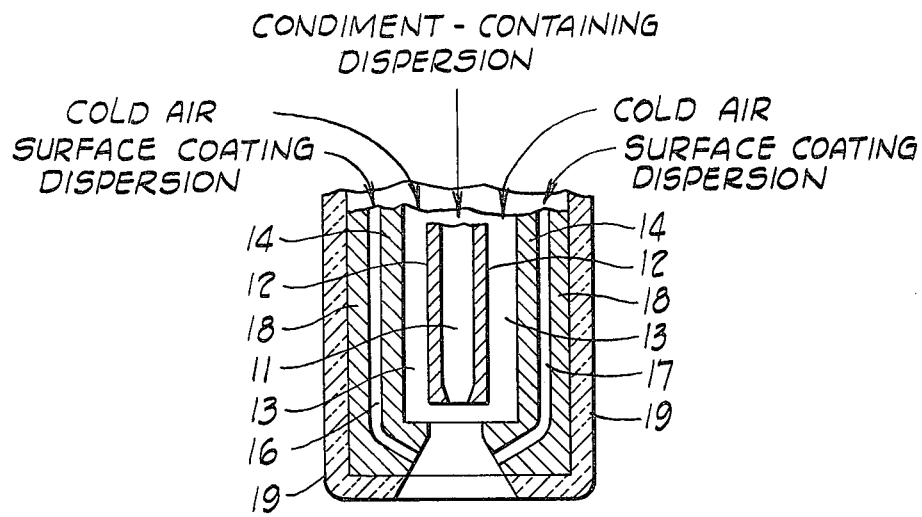

United States Patent
Johnson et al.

[11] 3,949,096
[45] Apr. 6, 1976

[54] SPRAY DRYING PROCESS FOR ENCAPSULATION OF CONDIMENT PARTICLES

[75] Inventors: Lawrence A. Johnson, Medina, Ohio; Edgar J. Beyn, Annapolis, Md.

[73] Assignee: SCM Corporation, New York, N.Y.

[22] Filed: July 31, 1974

[21] Appl. No.: 493,327

[52] U.S. Cl. ............. 426/302; 426/285; 426/294; 426/471
[51] Int. Cl.² .......................................... A23L 1/22
[58] Field of Search ......... 426/310, 99, 89, 302, 96, 426/93, 294, 309, 444, 467, 470, 305, 342, 471, 285; 209/11; 55/83, 261; 34/13, 10, 578; 117/100 A

[56] References Cited
UNITED STATES PATENTS

| | | | |
|---|---|---|---|
| 2,851,786 | 9/1958 | Scherer | 34/13 X |
| 2,910,386 | 10/1959 | Lachmann | 426/302 X |
| 3,063,848 | 11/1962 | Gelder | 426/467 X |
| 3,112,220 | 11/1963 | Heiser et al. | 426/302 X |
| 3,121,639 | 2/1964 | Bauer et al. | 426/471 X |
| 3,208,951 | 9/1965 | Berger et al. | 117/100 A X |
| 3,389,000 | 6/1968 | Fujiba et al. | 426/99 |
| 3,621,902 | 11/1971 | Okada et al. | 426/471 X |
| 3,647,480 | 3/1972 | Cermak | 426/342 X |
| 3,697,286 | 10/1972 | Gruh | 426/302 |
| 3,796,814 | 3/1974 | Cermak | 426/98 |

Primary Examiner—S. Leon Bashore
Assistant Examiner—Kenneth M. Schor
Attorney, Agent, or Firm—Jerry K. Mueller, Jr.

[57] ABSTRACT

An improvement in process for producing encapsulated condiment particles by spray drying wherein said spray-dried particles are cooled while they are maintained in gas-suspended condition in order to prevent them from agglomerating upon collection.

The process involves contacting a first spray of particles with cold air to assist in atomizing it; then spraying a second particle stream which contacts the first. The particle stream which is formed, is then discharged through a heating zone, after which it is cooled while being maintained in a gas suspended condition. Finally, the resulting coated particles are separated from the gas.

2 Claims, 2 Drawing Figures

SPRAY DRYING PROCESS FOR ENCAPSULATION OF CONDIMENT PARTICLES

This application is cross-referenced to the following application filed on even date herewith: Lawrence A. Johnson and Edgar J. Beyn, Ser. No. 493,325, entitled "Condiment Encapsulation by Spray Drying". The disclosure of said application is expressly incorporated herein by reference.

This invention relates to an improvement in process for producing condiment particles by spray drying, and more particularly such process wherein such dried particles are rendered resistant to agglomeration.

The most pertinent prior art known to applicants is the above-referenced application. It shows the production of condiment particles by spray drying wherein a spray of condiment-containing dispersion is intercepted by and coated with an edible surface coating dispersion that is convertible by heat into a surface coating.

Advantages of this improvement over prior proposals include the fact that at least the surface of the product particles is cooled (usually substantially hardened) while the particles are in gas-suspended condition before they can block, cake or agglomerate appreciably. Additionally, the core can be congealed or partially congealed simultaneously with the cooling of the surface coating if said core is congealable (solidifies) at the chilling zone temperature.

The instant invention is an improvement in process for producing condiment particles wherein particles of a first spray containing said condiment are intercepted by and coated with a further spray of edible coating dispersion that is convertible by heat into a dry surface coating and the resulting composite particles are dried while they are suspended in a current of gas in a heating zone. Such improvement comprises: discharging said current with suspended particles from said heating zone; mixing said discharged current with a flow of cold gas sufficient for substantially cooling said suspended particles while maintaining them in gas-suspended condition; and separating resulting cooled particles from gas entraining same.

FIG. 1 shows a useful nozzle tip assembly in cross-sectional elevation. The condiment-containing dispersion flows through passage 11, which passage is defined by tube wall 12. Annular to tube wall 12 is passage 13 conveying cold air transverse to the jet of condiment-containing dispersion exiting from passage 11 and atomizing this jet. Annular passage 13 is defined by tube wall 12 and the inner wall of interior casing 14.

A pair of peripheral passages 16 and 17 (180° opposed and small in diameter) convey the surface coating dispersion through exterior casing 18 and discharge it as a spray into the zone of atomized condiment-containing dispersion. There can be additional such peripheral passages, generally opposed to each other and tending to intersect if unimpeded into a conical pattern looking down, but when the nozzle is in full operation, the surface coating dispersion is atomized quite thoroughly and additional such streams of surface coating dispersion tend to make more perfect coatings on the core particles rich in condiment. Lagging 19 insulates the nozzle assembly from substantial heat loss. Obviously, more than one kind of surface-coating dispersion can be used for the coating spray, each projected from a different spraying outlet.

Figure 2:
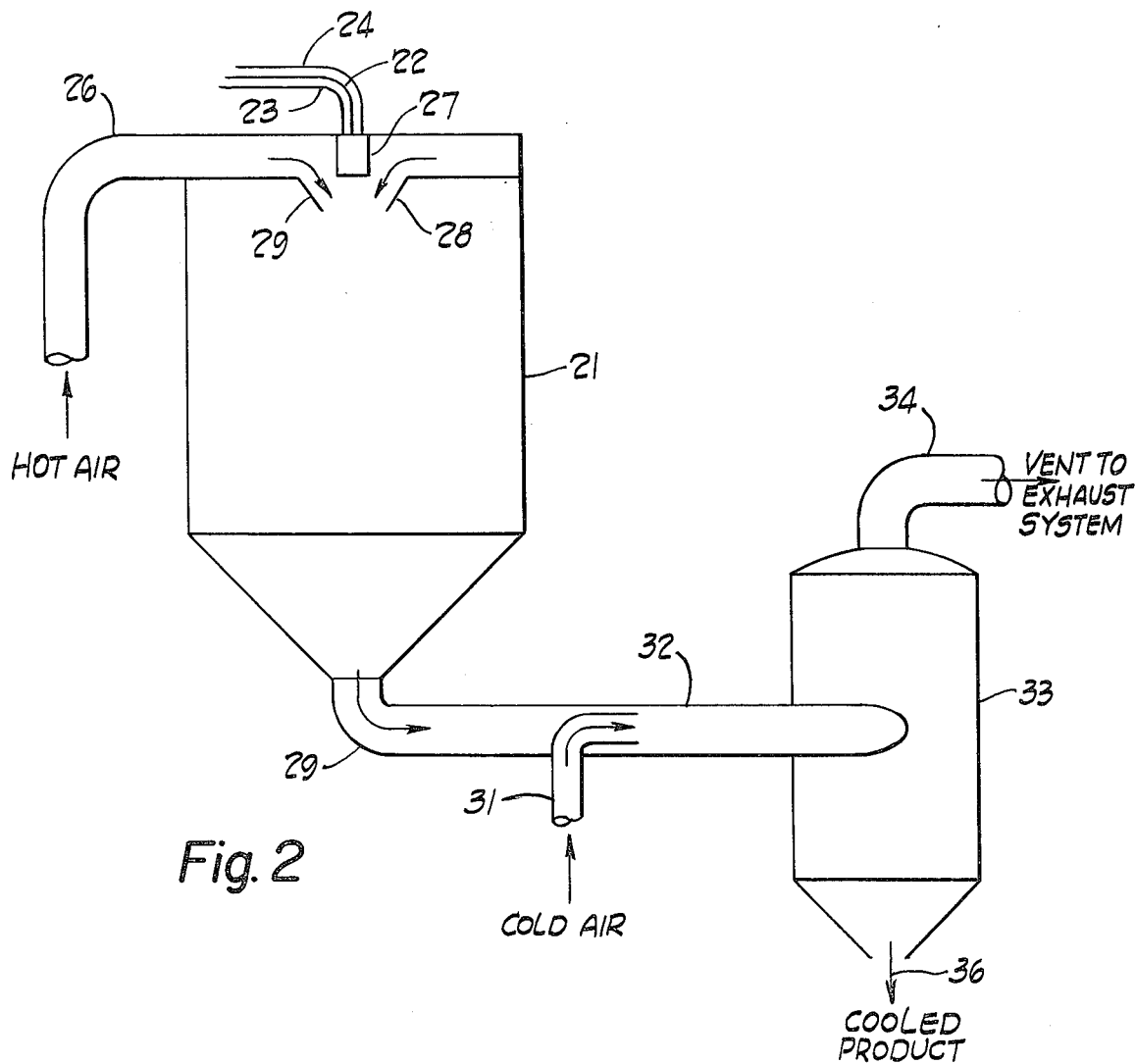

FIG. 2 shows a typical spray dryer for this process schematically in vertical cross-section elevation. Shell 21 (the heating zone) is composed of a vertical cylindrical body with a tapered base. Hot air is fed into line 26 and is at a suitable temperature and flow rate for drying at least the surface coating dispersion that coats the spray particles of condiment-containing dispersion. Typically the hot air will range in temperature from about 200° to about 400°F. Hot air from line 26 enters shell 21 through passages defined by louvers 28 and 29, which louvers are positioned for causing the hot air and coated particles to swirl in and down through said heating zone 21. Condiment-containing dispersion enters the apparatus through line 22 along with an atomizing flow of air through line 23 and surface-coating dispersion through line 24. These are discharged inwardly into shell 21 through nozzle 27, typically a nozzle like that shown in FIG. 1.

The surface coating dispersion dries as the particles flow cocurrently with the hot air in the heating zone. The current of suspended particles (typically at about 100° to 200°F.) is discharged through outlet 29 located at the tapered base of shell 21 and is mixed in chilling zone 32 with a flow of cold air which enters said chilling zone through inlet 31. The spent gas and entrained cooled particles pass from chilling zone 32 into cyclone separator 33 wherein the cooled product is separated from the spent gas. Cooled product is discharged through outlet 36 located at the base of said separator and collected. Spent gas is withdrawn through vent outlet 34 located at the top of said separator and passed to a conventional exhaust system (not shown). Additionally, the product can be dried further and/or cooled by gas fluidization.

The spray dryer can be operated under superatmospheric or subatmospheric pressure, although atmospheric pressure whenever feasible is preferred for efficiency and economy.

A condiment for purposes of this invention can be a liquid, vapor, or solid phase seasoning, flavoring, salting, sweetening, souring, spicing, proteinaceous material, and/or coloring ingredient or ingredient mixture suitable for producing or enhancing a texture flavor and/or color in an edible product. It can include or consist of single or mixed pungent or spicy solids, flavoring oils, essences, oleoresins, extracts and other zesty flavorings, for example oleoresin of ginger, oils or extracts or solid forms of sage, pimenta, coriander, parsley, garlic, caraway, nutmeg, cardamon, cloves, celery, etc. It also can include or consist of: edible titanium dioxide in permissible amounts, especially those treated in accordance with U.S. Pat. Nos. 3,591,940 and 3,579,356; monosodium glutamate; frequently sticky or liquid or semi-liquid food emulsifiers or blends thereof, especially those blended with normally solid lipoidal material, such emulsifiers being one or more alkoxylated or plain partial glycerides of edible fatty acids, lecithin, hydroxylated lecithin, alkoxylated and plain glycol esters of edible fatty acids, ethoxylated or plain sorbitol or sorbitan esters of fatty acids, food emulsifiers in salt form such as calcium stearyl lactylic acid, edible gums, stabilizers, and other food ingredients such as gelatin, soy protein, sodium carboxymethyl cellulose, algin and its salts, edible microcrystalline cellulose, hydroxypropyl cellulose, dextrose, sucrose, hydrolyzed cereal solids corn syrup, sorbitol, mannitol, saccharin, caseinate and its salts, cornstarch, wheat flour, rice flour, breadcrumbs, and the like; milk and milk products in concentrated or dried form such as whole milk, non-fat milk, buttermilk, sweet cream, whey, butter oil, lactose or the like and mixtures thereof; egg albumin, soy protein, or like proteinaceous materials and mixtures thereof; lipoidal materials such as an edible vegetable fat, animal fat, so called "low molecular" fats, acetoglycerides, free higher ($C_{12-26}$) fatty acids, often blended with a fatty food emulsifier such as a monoglyceride, diglyceride or a partial glycolate of fatty-forming ($C_{12-26}$) fatty acids, glycerol mixed esters of water soluble hydroxy carboxylic and higher fatty acids, polyoxyalkylene derivatives of sorbitan esters of higher fatty acids, glycol esters of higher fatty acids and their polyoxyalkylene derivatives, higher fatty acid esters of polyglycerols and their polyoxyalkylene derivatives, tartaric acid esters of higher fatty acid esters of citric acid such as dipalmityl or distearyl citrate, sucrose esters of higher fatty acids, alkoxylated partial higher fatty esters of polyhydric alcohols having from 2 to 6 carbon atoms, and mixtures of same. Thus lipoidal material for the instant purpose includes triglycerides, fatty emulsifers, and mixtures of same.

If the condiment is highly volatile, or liquid, or normally vaporous, it can be blended with lipoidal material such as hard fat or sorbed on or in a solid and processed (under superatmospheric pressure where necessary or desirable) to retain it for handling and conversion into particulates.

The edible surface coating dispersion comprises an edible coating material dispersed in a fugitive carrier or solvent, e.g. water or ethanol, wherein the carrier or solvent can be volitized in the heating zone to leave a dry surface coating residue. Edible surface coatings include sacchariferous material, proteinaceous material, edible gums, colorants, normally solid lipoidal material (including a mixture of lipoidal materials), edible waxes, edible resins or like edible materials suitable for spray-coating core particles according to the precepts of this invention, and mixtures thereof.

Typical sacchariferous surface coating materials include sucrose, dextrose, hydrolyzed cereal solids corn syrup solids or other solids-forming sugars and mixtures thereof. Artificial sweeteners such as saccharine also can be used as at least a portion of the surface coating and can be considered sacchariferous for this use. The sacchariferous material alone can form the dry surface coating or it can be compounded with other surface coating lipoidal materials, proteinaceous materials, edible gums, edible resins, edible waxes or the like, and mixtures thereof.

Typical proteinaceous surface coating materials include milk and milk products in dried form such as whole milk, nonfat milk, buttermilk, whey, and lactose; egg albumin, casein and its salts, soy protein, algin and its salts or like proteinaceous materials, and mixtures thereof.

Edible gums and starches as the surface coating material can be guar gum, gum arabic, gum tragacanth, agar, carageen, dextrin or like edible gums, and mixtures thereof. Anticaking aids also can be included such as tricalcium phosphate and sodium aluminum silicate.

Edible waxes can be paraffin wax, beeswax, carnauba wax and like edible waxes, and mixtures thereof. Additionally, a glossy shine to the final composite particles (having a dry coating of materials other than wax) can be achieved by coating the interior wall of a heat-revolving pan with an edible wax and rolling the composite particles therein. The edible wax coats the particles thereby imparting the glossy shine to said particles.

Edible resins include shellac, methylcellulose, ethyl cellulose, terpene resins, carboxymethlycellulose and its salts, carboxyethylcellulose, hydroxy propylcellulose, hydroxyethylcellulose, hydroxypropylmethylcellulose, and certain synthetic carboxylic polymers such as carboxypolymethylene polymers neutralized with an appropriate amine or ammonia, or like edible resins and mixtures thereof.

Normally solid lipoidal material includes those lipoidal materials previously enumerated as suitable for use as the condiment including (but not limited to) edible vegetable fat, animal fat, so called "low molecular" fats, hard fatty acid, fatty food emulsifiers, etc. A solvent frequently is unnecessary when forming an edible surface coating dispersion of lipoidal material or mixtures thereof, as the lipoidal material can coat the condiment core in molten state in the heating zone to form a coating which can be hardened by cooling according to the precepts of this invention. Solvents help to thin such lipoidal material and can be useful for this purpose.

Additives which can be included as a fraction (typically a very minor fraction) of the lipoidal material condiment and/or coating include fungistats, bacteriostats, silicone oil, flavorants, odorants, anti-oxidants, tins, dyes, and colorants.

Preferably lipoidal material (including a mixture of lipoidal materials) used for the core and for the coating is normally solid. By a normally solid lipoidal material is meant that such material at 90°F., advantageously at 95°F., and preferably at about 110°–180°F. (with about 115°–120°F. being specially preferred) is ostensibly dry to the touch, free-flowing in small (for example 60–100 mesh) beaded form, and such beads do not tend to agglomerate strongly or appreciably or to deform appreciably even when standing unpacked to a depth of 6 inches high in a 1 inch diameter cylinder for 24 hours at 70°–80°F.

The edible surface coating dispersion additionally can be clored and/or flavored if desired. Thus, the final composite product can have the coating, the core or both colored and/or flavored either the same or in different combinations of coloring and flavoring.

The carrier or solvent portion of the edible surface coating dispersion can be water, a food-grade alcohol or like appropriate solvent. The solvent must be volitizable in the heating zone, ordinarily leaving at most an innocuous residue, and any such solvent residue deposited with the surface coating material must be ingestible.

In practicing this invention, the first step is to form and spray a dispersion containing the condiment. An already normally liquid condiment can be sprayed (atomized) in its liquid form for purposes of this step. A vaporous condiment to be coated is best dissolved or sorbed into a fluent, normally hard lipoidal material. Alternatively, such condiment can be sorbed on an edible solid and handled like a solid condiment. Certain solid condiments being coated can be melted in order to spray the condiment, provided that the desired organoleptic characteristics of such condiment are not grossly damaged by said melting. Alternatively and preferably, however, solid and most liquid condiments can be coated by dispersing them in finely divided state or dissolving them in a sprayable lipoidal matrix for efficiency and economy. Condiments which tend to swell upon exposure to moisture (for example, wheat flour) and those which are chemically activated by exposure to moisture (for example, moderate heat-resisting baking powder) are dispersed in finely divided state or dissolved in the sprayable lipoidal matrix so that any moisture content of the surface-coating dispersion does not so adversely affect or prematurely decompose them.

Forming a condiment-containing dispersion for the instant purpose means then converting (by melting, sorbing, dissolving or suspending) the condiment in such form that it can be atomized by conventional means, for example, airless spray, gas-assisted spray, spinning disc, or the like. Average particle size (diameter) for spraying can be as low as a few microns on up to 100 microns or even larger. While certain product particles preferably are at about 5 microns (average), many condiment products in our resulting spray-dried coated forms are advantageously of about 80–90 microns average diameter. Thus, the atomizing device, e.g., nozzle, used is made to produce such size, and solids sprayed are, of course, fine enough to preclude nozzle stoppage.

The spray containing the condiment is intercepted with a further spray of edible surface-coating dispersion convertible by spray drying into a dry surface coating. The multispray pattern usually is formed by use of a multicomponent spray nozzle. The resulting composite particles thereupon pass into a heating zone, therein drying the condiment core and coating simultaneously if both are dryable, otherwise, drying only the dryable dispersions. Such drying is accomplished by vaporization of volatile matter from the particles by hot gas, preferably hot air for efficiency and economy. The hot air preferably passes cocurrently with the coated particles in said heating zone for efficiency and economy. However, when the final particle size (effective diameter) becomes as large as 80–100 microns or larger, a countercurrent or cross flow heating gas stream can be employed appropriately. Thus, a heating gas stream can be countercurrent, cocurrent, or crosscurrent to the spray particles as is necessary or desirable (for example, to resist or promote classification).

The dry coated particles suspended in the current of hot air are discharged from the heating zone and mixed with a flow of cold gas (preferably cold air for efficiency and economy) in a chilling zone. The discharged current is generally at about 100°–200°F. and at such temperatures many coating materials can be somewhat tacky or sticky in this environment. The cooling of the particles is done while same are maintained in gas-suspended condition in order to minimize any such subsequent caking or blocking.

Accordingly, a sufficient flow of cold gas at a suitable temperature calculated to substantially cool the suspended particles is mixed with the discharged current from the heating zone in said chilling zone while the particles remain in such gas-suspended condition. For purposes of this application, substantial cooling is achieved when, upon collection of product particles and at the collection temperature, such product particles will resist appreciable blocking, caking and agglomeration, even when standing unpacked to a depth of 6 inches high in a 1 inch diameter cylinder for 24 hours. They will tend to be free-flowing.

The size (effective diameter) of the coated condiment particles and the proportion of condiment to surface coating material can be varied over a wide range. This is dependent upon the comdiment-containing dispersion spray particles sizes; the flow rates of the sprayed streams; and the concentration, and spray particle size and pattern of surface-coating material in the surface-coating dispersion. Final coated particles sizes can range from about 5 microns or smaller to 150 microns or larger. The weight proportion of condiment to surface-coating material in the dry coated particles ordinarily will range from about 0.11:1 to about 100:1 depending upon the intended usage of the coated particles. The size of and the condiment content in the coated particles each can be varied over the above ranges to produce particles of the desired size and condiment content, and particles can be classified as to size after production for particular use.

The coated particles of the instant process will have a condiment-laden core and a cooled, ostensibly dry coating thereon. Because some dry coatings can be hydratable upon exposure of the particles to moisture (for example, a sucrose coating) and thereby becoming sticky, it sometimes is necessary to handle and/or package the coated particles in the absence of humidified air or other moisture-containing sources and/or to include a dehumidifying material in the packaged product.

The condiment-laden core is afforded a measure of: protection (by the dry coating thereupon) against deterioration caused by exposure to the atmosphere; control for release of the condiment into a foodstuff or the like in which it is compounded, the surface coating dissolving to release the condiment at a desired rate rather than at an accidental juncture; prevention of undesired interaction between condiment and its surrounding materials in a food, drug, or cosmetic; and prevention of the condiment coloring and/or flavoring ingredient to bleach, run, dilute or evaporate. It is desirable, in some instances, that the coating serve only as a decorative (colored) and/or flavored coating, or in others as an aid in handling difficult-to-handle condiments, such as those that are sticky, liquid or semi-liquid under normal handling conditions. The amount of such protection is dependent upon the specific surface-coating material chosen, the coating thickness and the completeness of the coating on the condiment core. Ordinarily, there will be very little or no condiment at the surface of the coated particles, but even an incomplete coating is often adequate for many uses of the particles.

It should be noted that fines emanating from the spray pattern of condiment particles, generally such fines being most prominent at the periphery of such spray pattern, can be collected and aggregated into larger, more desirable sized particles by the spray of surface coating dispersion as it intersects the condiment spray. Such fines collection process is disclosed by the following application filed on even date herewith: Edgar J. Beyn docket number I-2106, Ser. No. 493,323, entitled "Equipment and Process for Spray Drying", which disclosure is expressly incorporated herein by reference.

Coating of the spray of condiment particles by the spray of surface coating dispersion can be improved additionally by subjecting each such spray to an equal but opposite electrostatic charge (for example, a positive charge to the condiment spray particles and a negative charge to the surface coating spray particles). Such oppositely charged spray particles would tend to be attracted to each other to further promote encapsulation of the condiment spray particles by the surface coating spray particles, especially if the condiment spray has a relatively higher surface tension than the surface coating dispersion has. U.S. Pat. No. 3,208,951 discloses such a method of encapsulation of a liquid (for example, water, glycerine or ethylene glycol) in aerosol form by an encapsulating substance (for example, a wax or synthetic resin) wherein the two sprays are given equal, but opposite electrostatic charges to produce 10–60 micron encapsulted particles. The disclose of said reference is expressly incorporated herein by reference.

The following example shows how the instant process can be practiced, but should not be construed as limiting the invention. In this specification, all parts are parts by weight, all percentages are weight percentages, and all temperatures are in degrees Fahrenheit unless otherwise expressly indicated.

EXAMPLE

Referring to FIG. 2, a molten blend of 10% five-fold orange oil and 90% of a 50% sucrose solution in water is introduced through line 22 at the rate of 100 ml./minute and temperature of 145°. Three SCFM (measured at 760 mm. Hg and 70°) of air at 70° passes through line 23. Edible shellac solution (10% in ethanol) passes through line 24 at the rate of 400 ml. per minute. These liquid flows are atomized in nozzle 27, said nozzle having a tip like that described in connection with FIG. 1. The net spray is directed downwardly and cocurrently into a flow of hot air (350°) entering shell 21 through louvers 28 and 29 at a rate of about 67 SCFM. This rate is adjusted in response to maintaining temperature of 200° sensed by a thermocouple positioned on the central axis of said shell 21 inches below the nozzle tip. The current of suspended particles is discharged through outlet 29 at temperature of about 100° and is mixed in chilling zone 32 with a flow of cold air (135 SCFM) at essentially atmospheric pressure, 40° and 10% relative humidity, which enters the chilling zone through inlet 31. The spent air and entrained cooled particles, essentially at 80°, pass from chilling zone 32 into cylcone separator 33 wherein the cooled product is separated from the spent air. The cooled, dry product, about 20 micron average particle size, is discharged through outlet 36 located at the base of said separator and collected. The spent gas is withdrawn through vent outlet 34 located at the top of said separator and passed to an exhaust system. The product is appreciably coated with sucrose enrobing a core rich in orange oil.

We claim:

1. In a process for producing condiment particles wherein particles of a first spray containing said condiment are intercepted by and coated with a second spray of edible coating material dispersed in a fugitive carrier, said coating material being convertible by heating into a dry surface coating at a temperature not greater than 400°F, and the resulting composite particles are dried while they are suspended in a current of gas in a heating zone, the improvement which comprises:
   flowing cold gas to assist in the atomizing of said first spray, before contacting said first spray with said second spray and then discharging said current of suspended particles from said heating zone;
   after said heating mixing said discharged current with a second flow of cold gas while maintaining them in gas-suspended condition; and separating resulting particles from gas entraining same;
   said second flow of cold gas being sufficient and cold enough for cooling said suspended particles sufficiently to resist appreciable agglomeration upon their collection.

2. The process of claim 1 wherein all the provided gases are air.

* * * * *